US012791567B2

(12) United States Patent
Verder et al.

(10) Patent No.: US 12,791,567 B2
(45) **Date of Patent: *Nov. 10, 2026**

(54) METHODS AND SYSTEM FOR USE IN NEONATAL DIAGNOSTICS

(71) Applicant: Sime Diagnostics Limited, London (GB)

(72) Inventors: Henrik Verder, Bagsværd (DK); Agnar Höskuldsson, Kgs. Lyngby (DK)

(73) Assignee: SIME DIAGNOSTICS LTD., London (GB)

( * ) Notice: Subject to any disclaimer, the term of this patent is extended or adjusted under 35 U.S.C. 154(b) by 1353 days.

This patent is subject to a terminal disclaimer.

(21) Appl. No.: 17/385,347

(22) Filed: Jul. 26, 2021

(65) Prior Publication Data

US 2021/0349111 A1 Nov. 11, 2021

Related U.S. Application Data

(63) Continuation of application No. 14/893,822, filed as application No. PCT/EP2014/060943 on May 27, 2014, now Pat. No. 11,105,822.

(30) Foreign Application Priority Data

May 27, 2013 (DK) ................................ 2013 70284

(51) Int. Cl.
*G01N 21/35* (2014.01)
*A61B 5/00* (2006.01)
(Continued)

(52) U.S. Cl.
CPC ............ *G01N 33/92* (2013.01); *A61M 16/04* (2013.01); *G01N 21/35* (2013.01); *A61B 5/0075* (2013.01);
(Continued)

(58) Field of Classification Search
CPC ....... G01N 2021/3595; G01N 2800/12; G01N 21/35; G01N 33/92; A61B 5/0075
See application file for complete search history.

(56) References Cited

U.S. PATENT DOCUMENTS 4,071,770 A * 1/1978 Shinitzky ............ A61B 5/0813 250/461.2
5,227,308 A * 7/1993 Jameson ............... G01N 33/92 436/907

(Continued)

OTHER PUBLICATIONS

Neligan et al., Working Party to Discuss Nomenclature based on Gestational Age and Birthweight, Archives of Disease in Childhood 45: 730, 1970 (Year: 1970).*

(Continued)

*Primary Examiner* — Jesse P Frumkin
*Assistant Examiner* — Theodore Charles Striegel
(74) *Attorney, Agent, or Firm* — Weston R. Gould; DINSMORE & SHOHL LLP

(57) ABSTRACT

The present invention concerns methods and tools for analysing biomarkers useful for diagnosing an individual, in particular a newborn, with a respiratory disease, especially a newborn suffering from respiratory distress syndrome (RDS). The method and tools of the invention can in one embodiment be used for very rapidly detecting the ratio between lecithin and sphingomyelin in very small body fluid samples, e.g. gastric aspirate of a newborn. The invention is thus useful for obtaining a rapid treatment of RDS by administration of surfactant.

11 Claims, 3 Drawing Sheets

(51) Int. Cl.
*A61M 16/04* (2006.01)
*G01N 33/92* (2006.01)

(52) U.S. Cl.
CPC . *G01N 2021/3595* (2013.01); *G01N 2800/12* (2013.01)

(56) References Cited

U.S. PATENT DOCUMENTS

| | | | | |
|---|---|---|---|---|
| 5,856,196 A * | 1/1999 | Alvarez | G01N 33/689 436/71 |
| 7,524,681 B2 | 4/2009 | Wolf et al. | |
| 11,105,822 B2 * | 8/2021 | Verder | A61M 16/04 |
| 11,781,980 B2 * | 10/2023 | Schousboe | G01N 33/487 514/789 |
| 2006/0286038 A1 * | 12/2006 | Rairkar | A61K 38/16 424/45 |
| 2023/0223150 A1 * | 7/2023 | Schousboe | G16H 50/20 600/300 |

OTHER PUBLICATIONS

Liu et al., Rapid determination of fetal lung maturity from infrared spectra of amniotic fluid, American Journal of Obstetrics & Gynecology 178(2): 234-241, Feb. 1998 (Year: 1998).*
Perkins et al., Fourier Transform Infrared Spectroscopy Part II Advantages of FT-IR, Journal of Chemical Education 64(11): A269-A271, Nov. 1987 (Year: 1987).*
Peneff et al., Determination of lecithin and sphingomyelin (L/S ratio) in gastric and/or pharyngeal aspirates of the newborn, Minerva Pediatrica (31)11: 835-840, Jul. 1979 (Year: 1979).*
Balint et al., Surfactant Lecithin Fatty Acid Composition and Its Relationship to the Infantile Respiratory Distress Syndrome, Pediatric Research 12: 715-719; published 1978 (Year: 1978).*
Bevilacqua, G. et al., "Prophylaxis of respiratory distress syndrome by treatment with modified porcine surfactant at birth: a multicentre prospective randomized trial", J. Perinat. Med., vol. 24, p. 1-12, 1996.
Kamper, J. et al., "Early treatment with nasal continuous positive airway pressure in very low-birth-weight infants", Acta Paediatr., vol. 82, p. 193-197, 1993.
Liu, K. et al., Prediction of RDS from amniotic fluid analysis: A comparison of the prognostic value of TLC and infra-red spectroscopy, Prenatal Diagnosis, 18: 1267-1275, 1998.
Polin, R. et al., "Newer experience with CPAP" , Semin Neonatol, vol. 7, p. 379-389, 2002.
Rodriguez, R. et al., Respiratory Distress Syndrome and its Management, Neonatal-perinatal medicine: Diseases of the fetus and infant, 7th ed., p. 1001-1011, 2002.
Sandri, F. et al., Prophylactic or early selective surfactant combined with nCPAP in very preterm infants, downloaded from pediatrics. aapublications.org at Danmarks Natur Og on Sep. 19, 2011.
Soll R.F., Prophylactic versus Selective Use of Surfactant in Preventing Morbidity and Mortality in Preterm Infants, Cochrane Review Update, Neonatology, 102: 169-171, Jul. 10, 2012.
Soll, R., Early versus delayed selective surfactant treatment for neonatal respiratory distress syndrome, Cochrane Database Syst. Rev. 4: CD001456, 1999.
Stevens, T. et al., Early surfactant adminstration with brief ventilation vs. selective surfactant and continued mechanical ventilation for preterm infants with or at risk for respiratory distress syndrome (review), the Cochrane Collaboration, Oct. 17, 2007.
Van Kaam, A. et al., Surfactant replacement therapy in preterm infants: A European survey, Neonatology, 100: 71-77, 2011.
Verder. H., Praenatal bestemmelse af lungematuriteten og forebyggelse af idiopatisk respiratory distress syndrom, Henrik Verder's doctoral dissertation: 1, 77, 78, 79 and 80, Nov. 1980.
Verder, H. et al., Surfactant Therapy and Nasal Continuous Positive Airway Pressure for Newborns with Respiratory Distress Syndrome, New England Journal of Medicine, 331:1051-1055, 1994.
Verder, H., Nasal Continuous Positive Airway Pressure and Early Surfactant Therapy for Respiratory Distress Syndrome in Newborns of Less Than 30 Weeks' Gestation, Pediatrics, 103(2): 1-6, Feb. 1999.
Verder, H., Nasal CPAP has become an indispensable part of the primary treatment of newborns with respiratory distress syndrome, Acta Paediatrica, 96: 482-484, 2007.
Liu et al., Rapid determination of fetal lung maturity from infrared spectra of amniotic fluid, American Journal of Obstetrics & Gynecology, 178(2): 234-241, 1998.
Liu et al., Comparison of infrared spectroscopic and fluorescence depolarization assays for fetal lung maturity, American Journal of Obstetrics and Gynecology, 183(1): 181-187, 2000.
Peneff, P., et al., Determination of lecithin and sphingomyelin (L/S ratio) in gastric and/or pharyngeal aspirates of the newborn, Minerva Pediatrica, Torino, 31(11): 835-840, 1979.
Borer, R. Jr. et al., Accuracy of gastric aspirate lecithin/ sphingomyelin ratio and chest roentgenogram in the diagnosis of RDS, Pediatric Research 8, 4: 444, 1974.
Brown. L. et al., Methods of Evaluation Fetal Lung Maturity, CRC Critical Reviews in Clinical Laboratory Sciences, 16(2): 85-159, DOI: 10.3109/10408368209107026.
Cavalieri, R. et al., Purification of lamellar bodies from human amniotic fluid, American Journal of Obstetrics and Gynecology, 150(4): 409-414, Oct. 15, 1984.
De La Cruz et al., Improved Thin-Layer Chromatographic Determination of Phospholipids in Gastric Aspirate from Newborns, for Assessment of Lung Maturity, Clinical Chemistry, 34(4): 736-738, 1998.
De Vries et al., A specific acid (alfa)-glucosidase in lamellar bodies of the human lung, Biochimica et Biophysica Acta, 837: 230-238, 1985.
De Vries et al., An improved procedure for the isolation of lamellar bodies from human lung. Lamellar bodies free of lysosomes contain a spectrum of lysosomal-type hydrolases, Biochemica et Biophysica Acta, 922: 259-269, 1987.
Dreissig, I. et al., Quantification of brain lipids by FTIR spectroscopy and partial least squares regression, Spectrochimica Acta Part A: Molecular and Biomolecular spectroscopy, 71(5): 2069-2075, 2009—XP025675194.
Engle, M. et al., Phospholipid Composition and Acyltransferase Activity of Lamellar Bodies Isolated from Rat Lung, Archives of Biochemistry and Biophysics, 173: 586-595, 1975.
Gerd Schmitz et al., Structure and fundction of lamellar bodies, lipid-protein complexes involved in storage and secretion of cellular lipids, Journal of Lipid Research, 32(10), pp. 1539-1570: 1991.
Hosafcr, G. et al., Clinical chemistry without reagents? An infrared spectroscopic technique for determination of clinically relevant constituents of body fluids, Analytical and Bioanalytical Chemistry, 387(5): 1815-1822, 2006, XP019488762.
Kuligowski, J. et al., Determination of lecithin and soybean oil in dietary supplements using partial least squares—Fourier transform infrared spectroscopy, Talanta, 77(1): 229-234, 2008, XP025430891.
Lee, W. et al., Pulmonary lamellar bodies in human amniotic fluid: Their relationship to fetal age and the lecithin/ sphingomyelin ratio, American Journal of Obstetrics and Gynecology, 136(1): 601-65, Jan. 1, 1980.
Oulton, M., The role of centrifugation in the measurement of surfactant in amniotic fluid, American Journal of Obstetrics and Gynecology, 135(3), Oct. 1, 1979.
Noble, D., FT-IR Spectroscopy: It's All Done With Mirrors, Analytical Chemistry, 67(11): 381A-385A, 1995.
Oulton, M. et al., Developmental Study of a Lamellar Body Fraction Isolated From Human Amniotic Fluid, Pediatr. Res., 14: 722-728, 1980.
Polin, R. et al., Newer experience with CPAP, Semin Neonatol, 7: 379-389, 2002.
Shaw, R. et al., Infrared spectroscopy of biological fluids in clinical and diagnostic analysis, Encyclopedia of analytic chemistry: applications, theory and instrumentaion: 24, 2006.
Stimac, T. et al., The influence of pre-eclampsia on fetal lung maturity, International Journal of Gynecology and Obstetrics, 118: 18-20, 2012.

(56) References Cited

OTHER PUBLICATIONS

Vandenbussche, G. et al., Secondary Structure and Orientation of the Surfactant Protein SP-B in a Lipid Environment. A fourier Transform Infrared Spectroscopy Study, Biochemistry, 31: 9169-9176, 1992.
Verder, H. et al., Early Surfactant Guided by Lamellar Body Counts on Gastric Aspirate in Very Preterm Infants, Neonatology, 104: 116-122, 2013.
Verder, H., Lamellar body counts on gastric aspirates for prediction of respiratory distress syndrome, Acta Pædiatrica ISSN 0803,5253, p. 715-180, 2011.
Armstrong et al., Predicting Respiratory Distress by Thin-Layer Chromatography of the Newborn Gastric Aspirate. Obstetrics and Gynecoloty, 48(1): 35-39, 1976.
Blumenfeld et al., Lecithin/Sphingomyelin ratios in tracheal and pharyngeal aspirates in respiratory distress syndrome; The Journal of Pediatrics, 85(3): 403-407, 1974.
Dcosta et al., Lecithin/Sphingomyelin Ratios in Tracheal Aspirates from Newborn Infants; Pediatric Research, 22(2): 154-157, 1987.
Gluck et al., Diagnosis of the respiratory distress syndrome by amniocentesis; Am J Obstet Gynecol., 109(3): 440-445, 1971.
Gotelli et al., Simultaneous Determination of Phosphatidylglycerol and the Lecithin/Sphingomyelin Ratio in Amniotic Fluid, Clin. Chem., 24(7): 1144-1146, 1978.
Mueller-Heubach et al., Lecithin/sphingomyelin ratio in amniotic fluid and its value for the prediction of neonatal respiratory distress syndrome in pregnant diabetic women; Am J Obstet Gynecol., 130(1): 28-34, 1978.
Mullett, Determination of drugs in biological fluids by direct injection of samples for liquid-chromatographic analysis, J. Biochem. Biophys. Methods, 70: 263-273, 2007.
St. Clair et al., The Probability of Neonathal Respiratory Distress Syndrome as a Function of Gestational Age and Lecithin/Sphingomyelin Ration, Am. J. Perinatol, 25(8): 473-480, Sep. 2008.
Sweet et al., European Consensus Guidelines on the Management of Neonatal Respiratory Distress Syndrome in Preterm Infants, Update Neonatology, 103: 353-368, May 31, 2013.
Touchstone et al., (3-sn-Phosphatidyl) cholines (Lecithins) in Amniotic Fluid, Clin. Chem., 29(11): 1951-1954 , 1993.

* cited by examiner

High accuracy

METHODS AND SYSTEM FOR USE IN NEONATAL DIAGNOSTICS

CROSS REFERENCE TO RELATED APPLICATIONS

This application is a continuation of U.S. patent application Ser. No. 14/893,822 filed Nov. 24, 2015, which is a U.S. National Stage application under 35 U.S.C. § 371 of PCT/EP2014/060943 filed May 27, 2014, and which depends from and claims priority to Denmark Application No. PA 2013 70284 filed May 27, 2013, the entire contents of each of which are incorporated herein by reference.

FIELD OF THE INVENTION

The present invention relates to the field of neonatal diagnostics and diagnosis and treatment of disorders of the newborn. The invention thus concerns the field of methods and tools for diagnosing Respiratory Distress Syndrome (RDS) of newborn, in particular in preterm infants.

BACKGROUND OF THE INVENTION

Surfactant deficiency at birth and development of Respiratory Distress Syndrome of newborn (RDS) is the most important cause of morbidity and mortality in preterm infants.

Respiratory Distress Syndrome

Respiratory Distress Syndrome (RDS) also called idiopathic respiratory distress syndrome (IRDS) or neonatal respiratory distress syndrome [1], and hyaline membrane disease (HMD), is a syndrome in premature infants caused by developmental insufficiency of surfactant production and structural immaturity in the lungs. It can also result from a genetic problem with the production of surfactant associated proteins. RDS affects about 1% of newborn infants and is the single leading cause of death and morbidity in preterm infants [2]. The incidence decreases with advancing gestational age, from about 50% in babies born at 26-28 weeks, to about 25% at 30-31 weeks. The syndrome is more frequent in infants of diabetic mothers, in the second born of premature twins, and in induced labours or caesarean sections.

The onset of RDS is shortly after birth, and is manifest by tachypnea, tachycardia, chest wall retractions (recession), expiratory grunting, nasal flaring and cyanosis during breathing efforts. As the disease progresses, the newborn may develop ventilatory failure (rising carbon dioxide concentrations in the blood), and prolonged cessations of breathing ("apnea"). Whether treated or not, the clinical course for the acute disease lasts about 2 to 5 days. During the first days the condition of the patient worsens and requires more support. Despite major advances in care, RDS remains the most common single cause of death in the first month of life. Complications include metabolic disorders (acidosis, low blood sugar), patent ductus arteriosus, low blood pressure, chronic lung changes, and intracranial hemorrhage. The disease is frequently complicated by prematurity and its additional defects in other organ function.

The characteristic histopathology seen in babies who die from RDS was the source of the name "hyaline membrane disease". Waxy-appearing layers of hyaline membrane line the collapsed alveoli of the lung. In addition, the lungs show bleeding, over-distention of airways and damage to the lining cells.

Moderate to severe cases of RDS will progress if the condition is not treated. Early nasal continuous positive airway pressure (nCPAP) decreases or halts the progression so that mechanical ventilation (MV) can be avoided in many cases [3-5].

In addition, about half of infants with RDS treated with nCPAP need surfactant supplementation to stop the progression [6, 7] as the lungs of infants with RDS are developmentally deficient of surfactant. Similarly, about 50% of infants treated with MV need surfactant [8]. These infants, in contrast to infants treated with nCPAP, often require more doses of surfactant for a sustained response [6].

Surfactant

Surfactant is a surface-active lipoprotein complex produced by specialized lung cells called Type II cells or Type II pneumocytes. The proteins and lipids that comprise the surfactant have both a hydrophilic region and a hydrophobic region. By adsorbing to the air-water interface of alveoli with the hydrophilic head groups in the water and the hydrophobic tails facing towards the air, the main lipid component of surfactant, dipalmitoylphosphatidylcholine (DPPC), reduces surface tension. In addition to DPPC which constitutes about 40%, the surfactant complex comprises about 40% other phospholipids, about 5% surfactant-associated proteins (SP-A, B, C and D) and additionally cholesterol and trace amounts of other substances.

The function of the surfactant complex is to increase pulmonary compliance, prevent atelectasis (collapse of the lung) at the end of expiration and to facilitate recruitment of collapsed airways.

Surfactant helps prevent collapse of the terminal airspaces throughout the normal cycle of inhalation and exhalation. The surfactant is packaged by the cell in structures called lamellar bodies, and extruded into the air-spaces. The lamellar bodies subsequently unfold into a complex lining of the air-space. This layer reduces the surface tension of the fluid that lines the air-space. Surface tension is responsible for approximately ⅔ of the elastic recoil forces. In the same way that a bubble will contract to give the smallest surface area for a given volume, so the air/water interface means that the liquid surface will tend towards being as small as possible, thereby causing the air-space to contract. By reducing surface tension, surfactant prevents the air-spaces from completely collapsing on exhalation. In addition, the decreased surface tension allows re-opening of the air-space with a lower amount of force. Therefore, without adequate amounts of surfactant, the air-spaces collapse and are very difficult to expand. Microscopically, a surfactant deficient lung is characterized by collapsed air-spaces alternating with hyper-expanded areas, vascular congestion and, in time, hyaline membranes. Hyaline membranes are composed of fibrin, cellular debris, red blood cells, rare neutrophils and macrophages. They appear as an eosinophilic, amorphous material, lining or filling the air spaces and blocking gas exchange. As a result, blood passing through the lungs is unable to pick up oxygen and unload carbon dioxide. Blood oxygen levels fall and carbon dioxide rises, resulting in rising blood acid levels and hypoxia. Structural immaturity, as manifest by decreased number of gas-exchange units and thicker walls, also contributes to the disease process. Therapeutic oxygen and positive-pressure ventilation, while potentially life-saving, can also damage the lung. The current diagnosis is based on the clinical condition supplemented by chest x-ray, which demonstrates decreased lung volumes (bell-shaped chest), a small (0.5-1 mm), discrete, uniform infiltrate (sometimes described as a "ground glass" appearance) that involves all lobes of the lung, and airbronchograms (i.e. the infiltrate will outline the larger airways passages which remain air-filled). In severe cases, this becomes exaggerated until the cardiac borders become inapparent (a 'white-out' appearance).

In pregnancies of greater than 30 weeks, the fetal lung maturity may be tested by sampling the amount of surfactant in the amniotic fluid by amniocentesis, wherein a sampling syringe needle is inserted through the mother's abdomen and uterus. Several tests are currently available that correlate the production of surfactant. One of the most important tests involves measurement of the concentration ratio between the phospholipids lecithin and sphingomyelin, the so called "L/S ratio". If the L/S ratio is less than about 2.0, this is an indication of that the fetal lungs are deficient [9].

A therapeutic standard procedure in very preterm infants has been to start with nCPAP, and, as surfactant is better administered early than late [6, 10, 11], to give surfactant during a short intubation as soon as clinical symptoms and an increasing oxygen requirement indicate moderate to severe RDS [6, 12]. This so-called INSURE (intubation surfactant extubation) procedure is now widely used and has resulted in diminished use of MV [10] and a decreased incidence of bronchopulmonary dysplasia (BPD) [11, 13]. Many infants are still given surfactant relatively late—typically the median age at treatment was 5 h [4]. Additionally, common clinical criteria for identification of infants with RDS in need of surfactant and timing of this treatment are missing [14]. Consequently, there is a need for a rapid quantitative method to identify which of the very preterm infants who has a high risk of failing nCPAP and who therefore should receive surfactant at an early stage. Prophylactic surfactant treatment as an alternative has proven suboptimal [13]. Preferably the diagnosis and treatment should start immediately after birth. The present state of the art methods requires time-consuming laboratory tests to be performed thus delaying diagnosis and onset of medication of those in need thereof [15]. Additionally, the method of [15] is based on analysis of amnion fluid. While amnion fluid free from contaminants may be obtained in connection with caesarean delivery, it is difficult to obtain amnion fluid free from contaminants after vaginal delivery, thus compromising diagnostic accuracy. Hence there is a need for rapid analytical methods for diagnosing RDS after birth.

SUMMARY OF THE INVENTION

The present inventors have developed a method for determining the ratio between lecithin and sphingomyelin obtained from the newborn, without time-consuming laboratory preparations of the sample. The resulting ratio enables the clinician to determine if the infant is suffering from RDS. The speed and accuracy of the diagnostic method ensures that the appropriate medication can be commenced without delay, which is a critical factor for successful treatment of RDS.

Thus, in a first aspect the present invention concerns a method for diagnosing a respiratory disease of a subject, the method comprising the steps of:

a) providing a body fluid sample obtained from a subject,
b) determining in the sample of a), using analysis means, the amount of at least a first and at least a second group of compounds, wherein the first group of compounds is different than the second group of compounds,
c) obtaining a ratio between the first and the second group of compounds of b), d) correlating the ratio of c) with a control ratio, wherein a ratio differing from the control ratio is indicative of a respiratory disease of the subject.

The present method may be at least partly implemented in a computer. Thus, a further embodiment of the invention relates to computer implemented method for diagnosing a respiratory disease of a subject based on spectral data acquired from a body fluid sample obtained from said subject, the method comprising the steps of:

a) determining the activity and/or concentration of a first and a second group of compounds in said sample by analysing said spectral data, wherein the first group of compounds is different than the second group of compounds,
c) calculating a ratio between the activities and/or concentrations of the first and the second group of compounds,
d) correlating said ratio with a control ratio, wherein a ratio differing from the control ratio is indicative of a respiratory disease of the subject.

Thus, the present method may be may be integrated in a personal computer or it may be effectuated from a website, mobile phone, smartphone or other electronic device capable of executing computer code. A further embodiment of the invention therefore relates to a computer program product having a computer readable medium, said computer program product suitable for diagnosing a respiratory disease of a subject based on spectral data acquired from a body fluid sample obtained from said subject, said computer program product comprising means for carrying out all the steps of the herein disclosed method.

As time may be an issue in the diagnosis of the present invention, the diagnosis may advantageously be integrated in a diagnosis system that can be installed in hospital departments, such as the neonatal department, preferably in the delivery room. Such a system can integrate spectroscopy, analysis and disease indication that may provide a diseases indication within minutes after a biological sample has been obtained. A further embodiment of the invention therefore relates to a system for diagnosing a respiratory disease of a subject based a body fluid sample obtained from said subject, comprising

- a spectroscope for measuring spectral data from said sample,
- processing means configured for
  a) determining the activity and/or concentration of a first and a second group of compounds in said sample by analysing said spectral data, wherein the first group of compounds is different than the second group of compounds,
  b) calculating a ratio between the activities and/or concentrations of the first and the second group of compounds,
  c) correlating said ratio with a control ratio, and
  d) indicating whether the ratio is differing from the control ratio, wherein a predefined difference is indicative of a respiratory disease of the subject.

The system may be part of a health monitoring system as described in WO 2008/019695 disclosing a health monitoring service based on a central server, wherein the measurement of the biological samples are carried out as a local measurement and the measurement data are subsequently sent to a central server, where the data are processed and analysed, for example by expert knowledge systems, and a health profile is generated and sent back to the local system. Thus, the processing means may be fully or partly integrated in a central service remote from the local hospital department or even remote from the hospital. However, the processing means may also be fully integrated in the local system such that the system located in the hospital department includes spectrometer, spectral analysis and processing and disease indication.

Based on the diagnostic methods outlined herein above a rapid treatment of the individual in need thereof can be achieved, thus resulting in improved survival rate of the individual. The invention is in particular well suited for diagnosing and treating a newborn such as a premature infant.

Thus in one aspect the present invention concerns a method of treatment of RDS in a newborn individual, the method comprising the steps of:

a) providing a body fluid sample obtained from the newborn individual,
b) determining in the sample of a), using analysis means, the activity and/or concentration of a first and a second group of compounds, wherein the first group of compounds is different than the second group of compounds,
c) obtaining a ratio between the first and the second group of compounds of b),
d) correlating the ratio of c) with a control ratio, wherein a ratio differing from the control ratio is indicative of RDS of the subject,
e) if the ratio of d) is less than 2.0±0.5 administering a therapeutically effective amount of surfactant to the newborn individual.

In another aspect the present invention concerns a method of treatment of RDS in a newborn individual, the method comprising the steps of:

a) providing less than 100 μL, such as less than 95 μL, such as less than 90 μL, such as less than 85 μL, such as less than 80 μL, such as less than 75 μL, such as less than 70 μL, such as less than 65 μL, such as less than 60 μL, such as less than 55 μL, such as less than 50 μL, such as less than 45 μL, such as less than 40 μL, such as less than 35 μL, such as less than 100 μL, such as less than 30 μL, such as less than 25 μL, such as less than 20 μL, such as less than 19 μL, such as less than 18 μL such as less than 17 μL, such as less than 16 μL, such as less than 15 μL, such as less than 14 μL, such as less than 13 μL, such as less than 12 μL, such as less than 11 μL, such as less than 10 μL, such as less than 9 μL, such as less than 8 μL, such as less than 7 μL, such as less than 6 μL, such as less than 5 μL, such as less than 4 μL such as less than 3 μL, such as less than 2 μL, such as less than 1 μL, such as less than 0.9 μL, such as less than 0.8 μL, such as less than 0.7 μL, such as less than 0.6 μL, such as less than 0.5 μL, such as less than 0.4 μL, such as less than 0.3 μL, such as less than 0.2 μL, such as less than 0.1 μL of a body fluid sample obtained from the newborn individual,
b) determining in the sample of a), using analysis means, the activity and/or concentration of a first and a second group of compounds, wherein the first group of compounds is different than the second group of compounds,
c) obtaining a ratio between the first and the second group of compounds of b),
d) correlating the ratio of c) with a control ratio, wherein a ratio differing from the control ratio is indicative of RDS of the subject,
e) if the ratio of d) is less than 2.0±0.5, such as 2.0±0.4, such as 2.0±0.3, such as 2.0±0.2, such as 2.0±0.1, such as 2.0±0.05, administering a therapeutically effective amount of surfactant to the newborn individual.

In one aspect the invention concerns surfactant for use in a method of treatment of RDS in a newborn individual, the method comprising the steps of:

a) providing a body fluid sample obtained from the newborn individual,
b) determining in the sample of a), using analysis means, the activity and/or concentration of a first and a second group of compounds, wherein the first group of compounds is different than the second group of compounds,
c) obtaining a ratio between the first and the second group of compounds of b),
d) correlating the ratio of c) with a control ratio, wherein a ratio differing from the control ratio is indicative of RDS of the subject,
e) administering a therapeutically effective amount of the surfactant to the newborn individual, if the ratio determined in step d) is less than 2.0±0.5.

In one aspect the invention concerns use of surfactant for the preparation of a medicament for the treatment of RDS in a newborn individual comprising the steps of:

a) providing a body fluid sample obtained from the newborn individual,
b) determining in the sample of a), using analysis means, the activity and/or concentration of a first and a second group of compounds, wherein the first group of compounds is different than the second group of compounds,
c) obtaining a ratio between the first and the second group of compounds of b),
d) correlating the ratio of c) with a control ratio, wherein a ratio differing from the control ratio is indicative of RDS of the subject,
e) administering a therapeutically effective amount of the surfactant to the newborn individual, if the ratio determined in step d) is less than 2.0±0.5.

Step 1) includes providing a sample of gastric aspirate.

Step 2) comprises applying the sample to the instrument; placing a multi frequency infrared (IR) light beam through the sample; measures molecular light absorbance/luminescence in the infrared light frequency spectra; passing the raw absorbance spectrum data passed to processing unit.

Step 3) comprises processing raw data by Fourier Transform (FT) algorithm to produce light absorption wavelength.

Step 4) comprises extracting chemical information (lecithin and sphingomyelin concentration and/or activity) from spectral signatures through chemometrics algorithm (multivariate data analysis).

Step 5) comprises obtaining an L/S ratio and optionally a recommended treatment regime.

Figure 1:
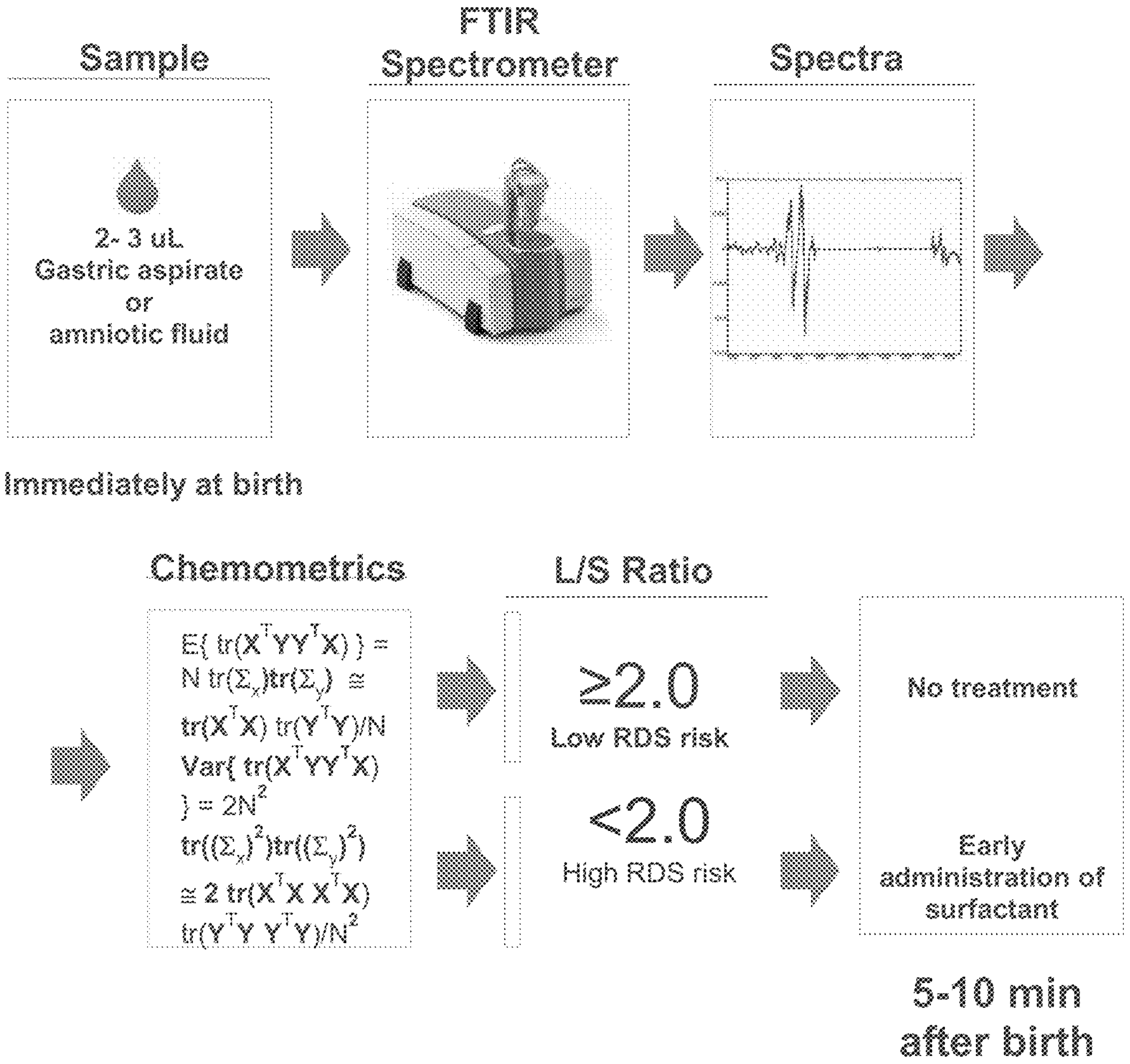
FIG. 1: Overview of method
Figure 2:
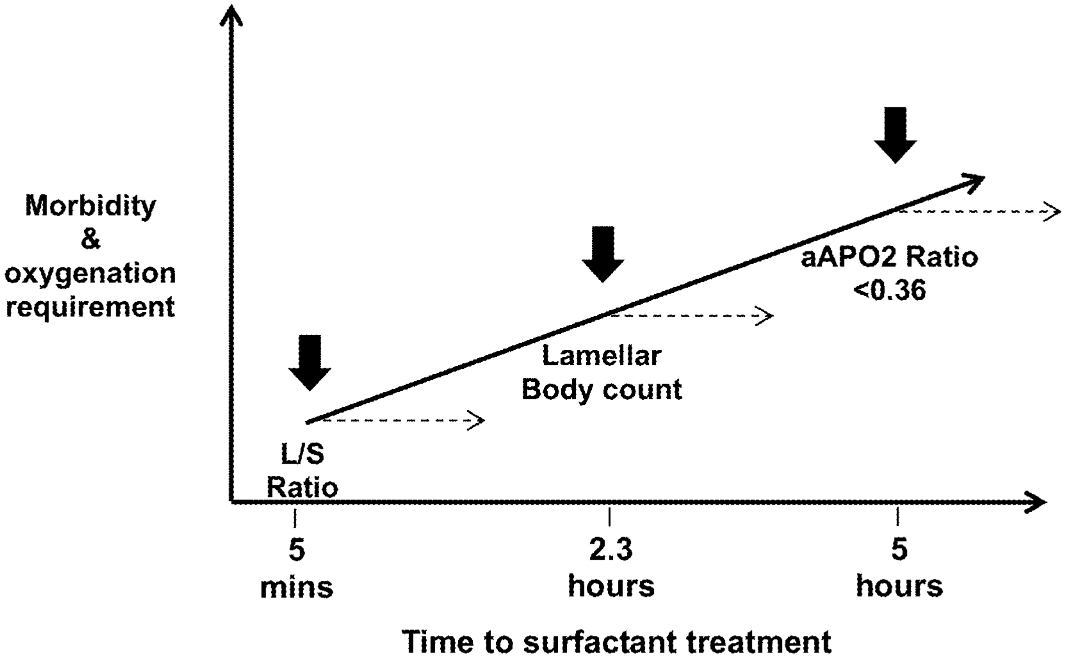

FIG. 2: Comparison of time to surfactant treatment of the method of the present invention, versus time to surfactant treatment of current state of the art techniques. The morbidity and oxygenation requirement increases significantly with time, and accordingly a rapid diagnosis of RDS is essential for minimising morbidity of newborn suffering from RDS.

Figure 3:
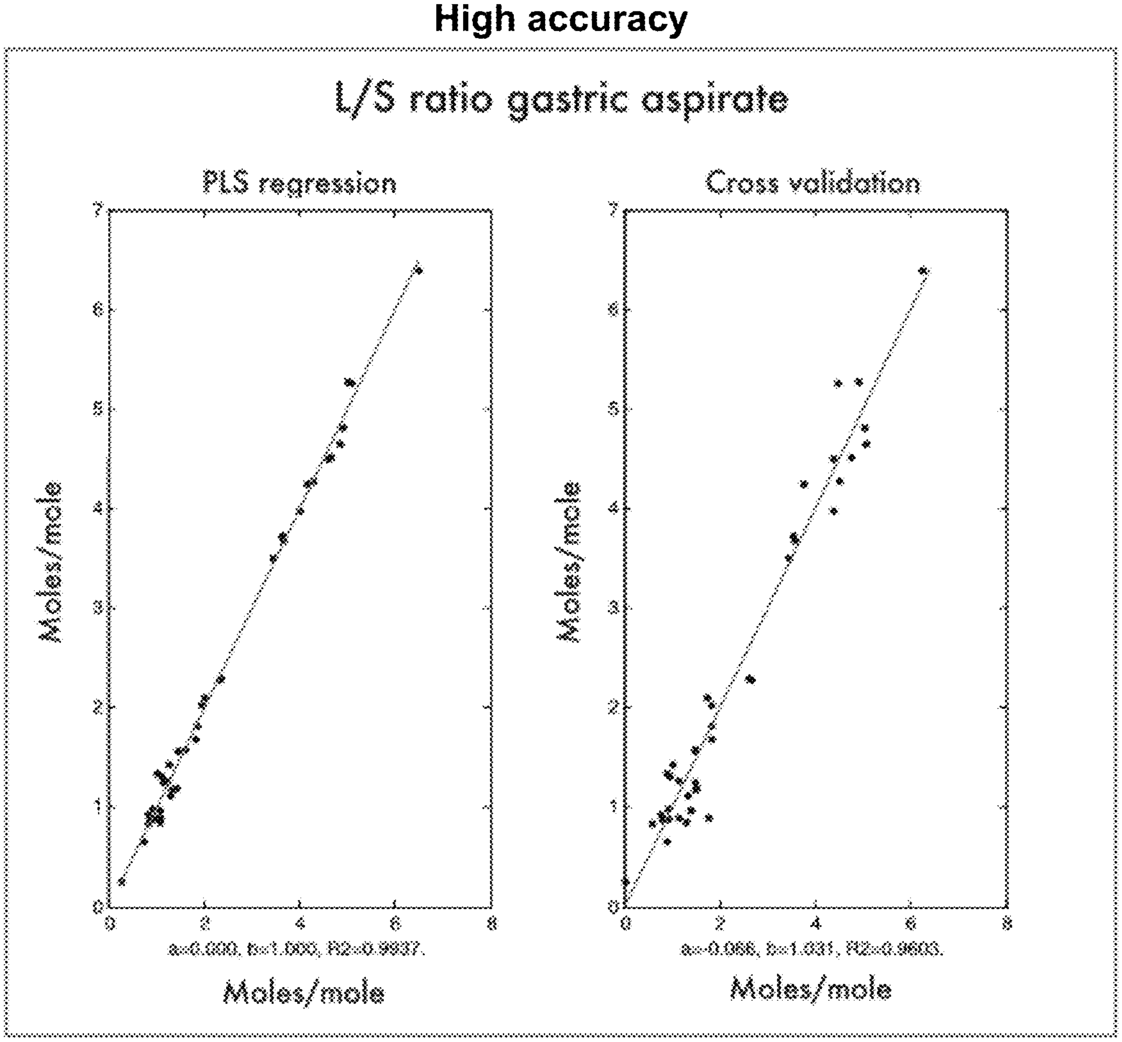

FIG. 3: In the figure to the left is shown the results of calibration. The $R^2$ value between measured and computed LS-ratio values is 0.99. The figure to the right shows the results of cross-validation. The $R^2$ value between the measured and cross-validated LS-ratio values is 0.96.

DETAILED DESCRIPTION OF THE INVENTION

Definitions

Analysis means: The term 'analysis means' as used herein refers to an instrument capable of detecting the physical property of a molecule or group of molecules. In one embodiment the analysis means is a FTIR spectrometer. Preferably the analysis means is a Bruker alpha FTIR spectrometer capable of performing measurements in very small sample volumes such as down to 1 μL.

Mid-IR: The term Mid-IR or Mid wavelength infrared, also called intermediate infrared (IIR) and mid-red FTIR spectroscopy as used herein refers to light having a wavelength of between about 3 to about 50 μm.

Premature infant: The term premature infant as used herein refers to an infant born before or up to 37 weeks into the pregnancy.

Respiratory distress syndrome of newborn: The term "Respiratory Distress Syndrome" as used herein refers to the term as understood by those of skill in the art. RDS may also be defined as P22.0 of WHO's ICD-10 disease classification. The abbreviation RDS stands for Respiratory Distress Syndrome.

Diagnostic Method

It is essential for the success of treatment of respiratory distress syndrome (RDS) in newborn premature infants, to rapidly assess the status of the development of the lungs of the infant. This can be performed by measuring the amount of lecithin and sphingomyelin. However, the methods known to date require sample preparation which is time consuming and thus delays commencement of medication by surfactant. The methods of the current state of the art furthermore rely on amniotic fluid which may be difficult to obtain in pure form during normal vaginal delivery.

The present inventors have found that an alternative to amniotic fluid is to obtain and measure the amount of lecithin and sphingomyelin in gastric aspirate obtained from the newborn. However, only very small volumes of gastric aspirate can be obtained from premature infants. Hence conventional methods known in the art cannot readily be applied to samples obtained from gastric aspirate.

The present inventors have addressed these two problems and found that it is possible to analyse very low volume samples from gastric aspirate obtained from the newborn individual and to determine the ratio between lecithin and sphingomyelin in the sample, without time-consuming laboratory preparations of the sample.

Thus in a main aspect the present invention concerns a method for diagnosing a respiratory disease of a subject, the method comprising the steps of:

a) providing less than 30 μL of a body fluid sample obtained from a subject,
b) determining in the sample of a), using analysis means, the amount of at least a first and at least a second group of compounds, wherein the first group of compounds is different than the second group of compounds,
c) obtaining a ratio between the first and the second group of compounds of b),
d) correlating the ratio of c) with a control ratio, wherein a ratio differing from the control ratio is indicative of a respiratory disease of the subject.

In one aspect the invention concerns a method for diagnosing RDS of a subject, the method comprising the steps of:

a) providing less than 30 μL of a body fluid sample obtained from a subject,
b) determining in the sample of a), using analysis means, the amount of at least a first and at least a second group of compounds, wherein the first group of compounds is different from the second group of compounds,
c) obtaining a ratio between the first and the second group of compounds of b),
d) correlating the ratio of c) with a control ratio, wherein a ratio differing from the control ratio is indicative of a respiratory disease of the subject.

The method of the present invention can be used for diagnosing any disorder associated with a biomarker measurable by the analysis means of the present invention. In one embodiment the respiratory disorder diagnosed by the method of the present invention is selected from the group consisting of respiratory distress syndrome, transient tachypnea of the newborn (TTN).

In a clinical setting, the physician utilising the present invention may, based on the result of the diagnostic method according to the present invention apply the method of exclusion, to determine if the subject from which the sample has been obtained, is suffering from RDS. If the result of the method indicates an L/S ratio significantly above 2.0, the subject does not suffer from RDS. If the clinician determine that the condition of the subject is severe, but that the L/S ratio is significantly above 2.0±0.5, the clinician can thus conclude that the subject is suffering from a critical condition other than RDS, and continue analysis and apply the appropriate treatment.

Thus, in one embodiment, the biomarker analysed by the analysis means of the invention is selected from the group consisting of phospholipids, fatty acids, proteins, lipoproteins and glycoproteins.

In one embodiment the first group of compounds is selected from the group consisting of phospholipids, fatty acids, proteins, lipoproteins and glycoproteins.

In one embodiment the second group of compounds is selected from the group consisting of phospholipids, fatty acids, proteins, lipoproteins and glycoproteins.

In one embodiment the second group of compounds comprises albumin, e.g. human serum albumin.

In one embodiment the first and the second compound are both phospholipids such as two different phospholipids. The first compound is typically lecithin and the second compound is typically sphingomyelin.

While the present invention aims at determining the ratio between a first and a second compound, such as lecithin and sphingomyelin respectively, further compounds or groups of compounds can be quantified either for analytical purposes or in order to compensate for background spectral noise. Thus in one embodiment the invention also concerns determining the amount of a third, fourth, fifth or further compound, such as a compound selected from the group consisting of phosphatidylglycerol, hemoglobin, apohemoglobin, hem and porphyrin. In particular, the third compound is hemoglobin.

In one embodiment the invention concerns the above defined method and a further step comprising subtracting the amount of the third compound from the amount of the first compound, thus obtaining a background corrected amount of the first compound.

Similarly, in one embodiment the invention concerns the above defined method and a further step comprising subtracting the amount of the third compound from the amount of the second compound, thus obtaining a background corrected amount of the second compound.

In another embodiment the invention concerns the above defined method and a further step comprising subtracting the amount of the third compound from the amount of both the first and the second compound, thus obtaining a background corrected amount of both the first and the second compound.

The amount of the compound or group of compounds can be determined by measuring the activity and/or the concentration of the compound or group of compounds.

The method of the present invention can be applied to any mammal, however in one embodiment the subject is a human being, e.g. an infant, such as a newborn.

The method is particularly suitable for analysing small sample volumes. Thus in one embodiment the infant is an infant, such as a premature infant born at 20 and 43 weeks gestation, such as between 20 and 42 weeks gestation, such as between 20 and 41 weeks, such as between 20 and 40 weeks, such as between 20 and 39 weeks gestation, such as between 21 and 38 weeks, such as between 23 and 37 weeks, such as between 24 and 37 weeks, such as between 25 and 37 weeks, such as between 26 and 37 weeks, such as between 27 and 37 weeks, such as between 28 and 37 weeks, such as between 29 and 38 weeks, such as between 30 and 39 weeks, such as between 31 and 39 weeks, such as between 32 and 39 weeks, such as between 33 and 39 weeks, such as between 34 and 39 weeks, such as between 35 and 39 weeks, such as between 36 and 39 weeks, such as between 37 and 39 weeks, such as between 38 and 39 weeks, such as between 38 and 40 weeks such, such as between 38 and 41 weeks, such as before 42 weeks gestation, such as before 43 weeks gestation.

It is advantageous to perform the analysis as rapidly as possible after birth in order to commence medication as soon as possible if applicable. Thus in one embodiment the sample is obtained from a newborn less than 24 h postnatal, preferably less than 20 h postnatal, more preferably less than 12 h postnatal, more preferably less than 5 h postnatal, more preferably less than 4 h postnatal, more preferably less than 3 h postnatal, more preferably less than 2 h postnatal, more preferably less than 1 h postnatal, more preferably less than 30 minutes postnatal, more preferably less than 20 minutes postnatal, more preferably less than 10 minutes postnatal, more preferably less than 5 minutes postnatal, more preferably less than 4 minutes postnatal, more preferably less than 3 minutes postnatal, more preferably less than 2 minutes postnatal, more preferably less than 1 minute postnatal.

While various biomarkers can be obtained from various body fluids or tissues depending on the purpose, it is preferred that the sample is obtained from gastric aspirate when the first group of compounds is lecithin and the second group of compounds is sphingomyelin. In one embodiment the body fluid is selected from the group consisting of gastric aspirate, tracheal fluid, hypopharyngeal secretion, amniotic fluid, blood, serum and plasma. In a preferred embodiment the body fluid is gastric aspirate.

If the sample is obtained from amniotic fluid, care should be taken to prevent contamination of the amniotic fluid. In one embodiment, the sample is obtained from a subject, such as a human being e.g. a female, such as a pregnant female.

The chances of collecting non-contaminated or essentially non.contaminated amniotic fluid are good in connection with caesarean sectioning. Thus in one embodiment the subject is a female human being, undergoing, or immediately about to undergo, caesarean sectioning. In a further embodiment the body fluid sample is amniotic fluid collected from the female human being, during or immediately subsequent to the caesarean sectioning.

As mentioned above, the present method allows for very small sample volumes. Thus in one embodiment the sample volume is less than 100 μL, more preferably less than 90 μL, more preferably less than 80 μL, more preferably less than 70 μL, more preferably less than 60 μL, more preferably less than 50 μL, more preferably less than 45 μL, more preferably less than 40 μL, more preferably less than 35 μL, more preferably less than 35 μL, more preferably less than 30 μL, more preferably less than 25 μL, more preferably less than 20 μL, more preferably less than 19 μL, more preferably less than 18 μL, more preferably less than 17 μL, more preferably less than 16 μL, more preferably less than 15 μL, more preferably less than 14 μL, more preferably less than 13 μL, more preferably less than 12 μL, more preferably less than 12 μL, such as around or less than 10 μL body fluid, such as around or less than 9.5 μL body fluid, such as around or less than 9 μL body fluid, such as around or less than 8.5 μL body fluid, such as around or less than 8 μL body fluid, such as around or less than 7.5 μL body fluid, such as around or less than 7 μL body fluid, such as around or less than 6.5 μL body fluid, such as around or less than 6 μL body fluid, such as around or less than 5.5 μL body fluid, such as around or less than 5 μL body fluid, such as around or less than 4.5 μL body fluid, such as around or less than 4 μL body fluid, such as around or less than 3.5 μL body fluid, such as around or less than 3 μL body fluid, such as around or less than 2.5 μL body fluid, such as around or less than 2 μL body fluid, such as around or less than 1.5 μL body fluid, such as around or less than 1 μL body fluid, such as around or less than 0.9 μL body fluid, such as around or less than 0.8 μL body fluid, such as around or less than 0.7 μL body fluid, such as around or less than 0.6 μL body fluid, such as around or less than 0.5 μL body fluid, such as around or less than 0.4 μL body fluid, such as around or less than 0.3 μL body fluid, such as around or less than 0.2 μL body fluid, such as around or less than 0.1 μL body fluid.

A further advantage of the present method in relation to methods of the current state of the art is that no sample preparation is required prior to performing the analysis. Thus in one embodiment the body fluid sample is directly transferred from the subject by a sampling means, to the analysis means without intermediate sample preparation.

While it is an advantage for rapid diagnostic purposes to avoid sample preparation, in certain embodiments the method further comprises the step of filtering, centrifuging, ultrasound sonicating or diluting the sample prior to loading the sample onto the sampling means.

The analysis may be performed by any suitable analysis means known by those of skill in the art, however in a preferred embodiment the analysis means is a Fourier transform infrared (FTIR) spectrometer, such as a Bruker Alpha FT-IR Spectrometer, a Bruker Optics Tensor 27 FTIR spectrometer or a Perkin Elmer spectrometer or any spectrometer suitable for the purpose of the present invention i.e. a spectrometer capable of accommodating and accurately measuring very small sample volumes such as sample volumes down to 1 μl. The spectrometer may be equipped with accessory equipment depending on the purpose and specifics of the analysis. In one embodiment the analysis means further comprises a Micro Biolytic AquaSpe sample unit. In order to measure small volumes it is important to be able to appropriately load the sample in the optical path. In one embodiment the optical path length is between 5 and 10 μm such as 8.5 μm.

The method analysis means may be cooled to obtain optimal performance. Hence in one embodiment the analysis means comprises a nitrogen cooled mercury cadmium telluride detector unit. In one embodiment the analysis means further comprises a MicroBiolytics 45w53D*28H unit.

The wavelength of the analysis means may be altered. In one embodiment the amount of the first, second and/or third group of compounds is determined in the mid-wavelength infrared range by an FTIR spectrometer.

Computer Implemented Method

The present method may be at least partly implemented in a computer. Thus, a further embodiment of the invention relates to computer implemented method for diagnosing a respiratory disease of a subject based on spectral data acquired from a body fluid sample obtained from said subject, the method comprising the steps of:

a) determining the activity and/or concentration of a first and a second group of compounds in said sample by analysing said spectral data, wherein the first group of compounds is different than the second group of compounds, c) calculating a ratio between the activities and/or concentrations of the first and the second group of compounds, d) correlating said ratio with a control ratio, wherein a ratio differing from the control ratio is indicative of a respiratory disease of the subject.

Thus, the present method may be may be integrated in a personal computer or it may be effectuated from a website, mobile phone, smartphone or other electronic device capable of executing computer code. A further embodiment of the invention therefore relates to a computer program product having a computer readable medium, said computer program product suitable for diagnosing a respiratory disease of a subject based on spectral data acquired from a body fluid sample obtained from said subject, said computer program product comprising means for carrying out all the steps of the herein disclosed method.

As time may be an issue in the diagnosis of the present invention, the diagnosis may advantageously be integrated in a diagnosis system that can be installed in hospital departments, such as the neonatal department, preferably in the delivery room. Such a system can integrate spectroscopy, analysis and disease indication that may provide a diseases indication within minutes after a biological sample has been obtained. A further embodiment of the invention therefore relates to a system for diagnosing a respiratory disease of a subject based a body fluid sample obtained from said subject, comprising a spectroscope for measuring spectral data from said sample, processing means configured for a) determining the activity and/or concentration of a first and a second group of compounds in said sample by analysing said spectral data, wherein the first group of compounds is different than the second group of compounds, b) calculating a ratio between the activities and/or concentrations of the first and the second group of compounds, c) correlating said ratio with a control ratio, and d) indicating whether the ratio is differing from the control ratio, wherein a predefined difference is indicative of a respiratory disease of the subject.

The system may be part of a health monitoring system as described in WO 2008/019695 disclosing a health monitoring service based on a central server, wherein the measurement of the biological samples are carried out as a local measurement and the measurement data are subsequently sent to a central server, where the data are processed and analysed, for example by expert knowledge systems, and a health profile is generated and sent back to the local system. Thus, the processing means may be fully or partly integrated in a central service remote from the local hospital department or even remote from the hospital. However, the processing means may also be fully integrated in the local system such that the system located in the hospital department includes spectrometer, spectral analysis and processing and disease indication.

Medical Uses/Methods of Treatment

Based on the diagnostic methods outlined herein above a rapid treatment of the individual in need thereof can be achieved, thus resulting in improved survival rate of the individual. The invention is in particular well suited for diagnosing and treating a newborn such as a premature infant.

Thus in one aspect the present invention concerns a method of treatment of RDS in a newborn individual, the method comprising the steps of:

a) providing less than 30 μL of a body fluid sample obtained from the newborn individual, b) determining in the sample of a), using analysis means, the activity and/or concentration of a first and a second group of compounds, wherein the first group of compounds is different than the second group of compounds, c) obtaining a ratio between the first and the second group of compounds of b), d) correlating the ratio of c) with a control ratio, wherein a ratio differing from the control ratio is indicative of RDS of the subject, e) if the ratio of d) is less than 2.0±0.5 administering a therapeutically effective amount of surfactant to the newborn individual.

In one aspect the invention concerns surfactant for use in a method of treatment of RDS in a newborn individual, the method comprising the steps of:

a) providing less than 30 μL of a body fluid sample obtained from the newborn individual, b) determining in the sample of a), using analysis means, the activity and/or concentration of a first and a second group of compounds, wherein the first group of compounds is different than the second group of compounds, c) obtaining a ratio between the first and the second group of compounds of b), d) correlating the ratio of c) with a control ratio, wherein a ratio differing from the control ratio is indicative of RDS of the subject, e) administering a therapeutically effective amount of the surfactant to the newborn individual, if the ratio determined in step d) is less than 2.0±0.5.

In one aspect the invention concerns use of surfactant for the preparation of a medicament for the treatment of RDS in a newborn individual comprising the steps of:

a) providing less than 30 μL of body fluid sample obtained from the newborn individual, b) determining in the sample of a), using analysis means, the activity and/or concentration of a first and a second group of compounds, wherein the first group of compounds is different than the second group of compounds, c) obtaining a ratio between the first and the second group of compounds of b), d) correlating the ratio of c) with a control ratio, wherein a ratio differing from the control ratio is indicative of RDS of the subject, e) administering a therapeutically effective amount of the surfactant to the newborn individual, if the ratio determined in step d) is less than 2.0±0.5.

While the critical ratio for determining if the subject is suffering from RDS typically is 2.0, the critical ratio between lecithin and sphingomyelin may be 1.5, 1.6, 1.7, 1.8, 1.9, 2.0, 2.1, 2.2, 2.3, 2.4 or 2.5 under which critical ratio the subject is considered to suffer from Respiratory distress syndrome (RDS).

REFERENCES

1. Dorland's Medical Dictionary—"Neonatal respiratory distress syndrome"
2. Rodriguez R J, Martin R J, and Fanaroff, A A. (2002) Neonatal-perinatal medicine: Diseases of the fetus and infant; 7th ed. (2002):1001-1011. St. Louis: Mosby.
3. Kamper J, Wulff K, Larsen C, Lindequist S. (1993) Acta Paediatr; 82:193-197.
4. Polin R A, Sahni R. (2002) Semin Neonatol 7:739-789.
5. Verder H. (2007) Acta Pdiatr 96:482-484.
6. Verder H, Albertsen P, Ebbesen F, Greisen G, Robertson B, Bertelsen A, Agertoft L, Djernes B, Nathan E, Reinholdt J. (1999) Pediatrics 103:e24.
7. Sandri F, Plavka R, Ancora G, Simeoni U, Stranak Z, Martinelli S, Mosca F, Nona J, Thomson, M, Verder H, Fabbri L, Halliday H. (2010) Pediatrics 125:e140.
8. Bevilacqua G, Parmagiani S, Robertson B. (1996) J Perinat Med 24:1-12.
9. Verder H., "Prænatal bestemmelse af lungematuriteten og forebyggelse af idiopatisk respiratory distress syndrom. Lecithinsphingomyelin ratio i amnionvæken" Doctoral dissertation 27 Nov. 1980 at University of Copenhagen.
10. Soll R F. (1999) Cochrane Database Syst Rev 4:CD001456.
11. Stevens T P, Blennow M, Meyers E H, Soll R. (2007) Cochrane Database Syst Rev 2007; 4: CD003063.
12. Verder H, Robertson B, Greisen G, Ebbesen F, Albertsen P, Lundstrøm K, Jacobsen T. (1994) N Engl J Med 331:1051-1055.
13. Soll R F. (2012) Neonatology 102:169-171.
14. Van Kaam A H, Jaegere A P, Borensztajn D, Rimensberger P C (2011) Neonatology 100:71-77.
15. Liu K-Z, Dembinski T C, Mantsch H H (1998) Prenatal Diagnosis 18: 1267-1275

EXAMPLES

Background

The present background section recapitulates the state of the art:

Moderate-severe RDS will progress untreated

Early surfactant is better than late and prophylaxis is suboptimal

Common criteria for identification of infants with RDS who need surfactant and timing of this treatment are missing There is need for a rapid method to identify which infants have a need for surfactant and should be given this treatment early Existing Methods for "the Timing"

Gestational age is not useful (only 50% of infants <30 wk.'s need surfactant)

FiO2 and oxygen saturation levels are not ideal and are not closed linked to oxygen tension level a/APO2 and similar useful parameters are not always available and time to diagnosing is too long (≥5 h in median)

Microbubble test, lamellar body counts and the like lung maturity tests performed on gastric aspirate (GAS) are sensitive to dilution or are depending of relative high volumes and individual expertise By using lamellar body counts as indicator of lung maturity and early surfactant therapy in very preterm newborns, it is possible to reduce the need for oxygen supplementation and to better the oxygenation at 6 h and 28 days of life Lecithin-Sphingomyelin [L/S]-Ratio The method is not sensitive to dilution and L/S-ratio <2.0 in amniotic fluid is correlated to development of RDS with high sensitivity and specificity L/S-ratio on GAS is also correlated to development of RDS Previous L/S methods have been performed by thin-layer chromatography (TLC) with results after ≥4 h L/S-ratio performed on GAS measured by Fourier Transform Infra-red Spectroscopy (FTJR) may be performed on small volumes and is a very quick method

Example 1: Timing of Surfactant Treatment

Methods

Gastric aspirate from 40 newborns with gestational age 27 to 41 weeks were frozen at −20° C. and analysed later. Before analyses gastric aspirates were mixed in 5 sec by a vortex mixer, and 50 pl was placed in a Tensor 27 FTIR spectrometer from Bruker Optics with a BioATR unit from Micro Biolytics Inc.

Results

Different concentrations of lecithin and sphingomyelin assay kits from Cayman Chemical, AH-Diagnostics were measured by a Konelab Prime 30i instrument. The lecithin and sphingomyelin values were measured by the FTIR instrument with good results compared to the standard values. L/S-ratio was determined satisfactorily with R2 correlation between measured values and computed ones and R210-fold cross-validation.

Conclusion

L/S values measured by FTIR may be available within a few minutes and may be used in the delivery room as guide for surfactant treatment.

Example 2: Present Invention in a Clinical Setting

When a premature infant is born very early, treatment with oxygen and nCPAP is started. MV is only given to infants who can't breath (<5% of the prematures).

The next step is collection of gastric aspirate <45 minutes after birth via a feeding tube (CH 6-8) and a syrinx. Different positions of the tube should be tried in order to find sufficient amounts of gastric aspirate.

After the gastric aspirate sample has been obtained, measurement of the L/S ratio is performed spectroscopically, preferably already in the delivery room to save time. 1-3 μl of gastric aspirate is required. The L/S ratio is obtained within 5-10 minutes using the method of the present invention. A L/S ratio less than about 2.0, such as below 1.8-2.2, e.g. below 1.9-2.1, e.g. below 1.5-2.5 indicates immature lungs and development of RDS, and hence the patient should obtain surfactant treatment. The best clinical results are obtained if the surfactant is administered as soon as possible after birth.

After diagnosing the patient with immature lungs and development of RDS using the method of the present invention, surfactant is administered to the patient. The main method of administering surfactant is INSURE to infants treated with nCPAP, while for infants treated with MV, surfactant is administered in the intratracheal tube e.g. via a thin catheter and syrinx.

The invention claimed is:

1. A method of treatment of respiratory distress syndrome (RDS) in a newborn individual, the method comprising the steps of:

a) providing a body fluid sample obtained from a newborn subject, wherein the body fluid sample is gastric aspirate, tracheal fluid or hypopharyngeal secretion, b) determining, using a spectrometer, in the sample of step a) the activity and/or concentration of a first compound and a second compound, wherein the first compound is lecithin or saturated lecithin and the second compound is sphingomyelin, c) obtaining a ratio between the first compound and the second compound of step b), d) correlating the ratio of step c) with a control ratio, wherein a ratio differing from the control ratio is indicative of RDS of the subject, e) identifying an individual with the ratio of step c) less than 2.0±0.5, and f) administering a therapeutically effective amount of surfactant to the newborn subject with said ratio, wherein steps a) to e) are collectively performed in less than 10 minutes.

2. The method according to claim 1, further comprising determining an activity or concentration of a third compound.

3. The method according to claim 2, wherein the third compound is selected from the group consisting of phosphatidylglycerol, hemoglobin, apo-hemoglobin, heme and porphyrin.

4. The method according to claim 2, wherein the third compound is hemoglobin.

5. The method according to claim 2 further comprising the step of subtracting the activity or concentration of the third compound from the activity or concentration of the first compound, thus obtaining a background corrected amount of the first compound.

6. The method according to claim 2 further comprising the step of subtracting the activity or concentration of the third compound from the activity or concentration of the second compound, thus obtaining a background corrected amount of the second compound.

7. The method according to claim 2 further comprising the step of subtracting the activity or concentration of the third compound from the activity or concentration of both the first and the second compound, thus obtaining a background corrected amount of both the first and the second compound.

8. The method according to claim 1, wherein the subject is a human infant born before 43 weeks gestation.

9. The method according to claim 1, wherein the body fluid sample is directly transferred from the subject to the spectrometer without intermediate sample preparation.

10. The method of claim 1, wherein the spectrometer is a Fourier transformed infrared (FTIR) spectrometer.

11. The method of claim 1, wherein the body fluid sample is gastric aspirate.

* * * * *